United States Patent [19]
Reeves et al.

[11] Patent Number: 5,961,479
[45] Date of Patent: Oct. 5, 1999

[54] THERAPEUTIC MASK

[75] Inventors: William Hatton Reeves, Pompano Beach, Fla.; Juan Abel Brignardelli, Buenos Aires, Argentina

[73] Assignee: Dermalabs Inc., Miami Beach, Fla.

[21] Appl. No.: 09/092,769

[22] Filed: Jun. 5, 1998

[51] Int. Cl.⁶ .................................................. A61F 13/00
[52] U.S. Cl. ............................... 602/41; 602/74; 602/48; 602/58
[58] Field of Search ............................. 602/48, 51, 41, 602/74, 17, 58

[56] References Cited

U.S. PATENT DOCUMENTS

| | | | |
|---|---|---|---|
| 4,117,837 | 10/1978 | Massó Remiro | 128/76 |
| 4,671,267 | 6/1987 | Stout . | |
| 4,738,257 | 4/1988 | Meyer et al. . | |
| 4,885,161 | 12/1989 | Cornell | 424/78 |
| 5,115,801 | 5/1992 | Cartmell et al. . | |
| 5,306,504 | 4/1994 | Lorenz | 424/449 |
| 5,633,256 | 5/1997 | Chen | 524/474 |

Primary Examiner—John G. Weiss
Assistant Examiner—Kelvin Hart
Attorney, Agent, or Firm—R. William Graham

[57] ABSTRACT

A therapeutic mask for application to a face of a patient suffering from facial wounds includes a relatively elastic substrate having a plurality of open surfaces defined therein of a predetermined size and spatially positioned with respect to one another to accommodate the patient's eyes, nose and mouth, a hydrogel substance having a plurality of open surfaces defined therein of a predetermined size and spatially positioned with respect to one another to accommodate the patient's eyes, nose and mouth and complimentarily connected to the elastic substrate such that the respective eyes, nose and mouth open surfaces align. The therapeutic mask further includes retaining straps connectable to the elastic substrate and of a size and configuration to extend about the head of the patient for supporting the therapeutic mask in a relatively fixed position on the patient's face.

8 Claims, 2 Drawing Sheets

THERAPEUTIC MASK

BACKGROUND OF THE INVENTION

1. Field of the Invention

The present invention relates to the field of hydrogel therapies for treating wounds wherein the hydrogel is employed as a humectant. More particularly, the present invention is directed to a therapeutic mask for treating wounds which result as part of a resurfacing procedure on a patient.

1. Related Art

There exist procedures and devices for treating wounds as a result of injury, ulceration, surgical incision, burns, paryngocutaneous fistulas or chemical burn of the skin. One known technique for treating and/or promoting healing of the skin employs the use of hydrogels which are multidimensional networks of hydrophillic polymers which interact with aqueous solutions to adsorb fluid exudate from the wound until reaching saturation or an equilibrium point. Such hydrogel therapies have included hydrogels made of polymers such as ethylene glycol, propylene glycol, dimethyl oxide, dimethyl formamide, poly-2-hydroxyethelymethacrylate, to name a few, and have been useful in treating such wounds wherein the hydrogel also significantly serves as a pseudo-skin during the healing process.

Other approaches have included the use of elasto-gel compositions which include a blend of glycerine as the humectant and hydrophobic polymers. The glycerin exhibited desirable bacteriostatic properties. Still others have made wound dressings having a hydrocolloid with pectin or carboxymethyl cellulose. Heretofore, these adsorbing substances have included a backing sheet or film to which the adsorbing substance is applied.

The control of water removal or loss from the injured skin is of major importance in the healing process. A problem which exists with such hydrogels is the inability of maintaining proper fluid adsorption to facilitate the healing process. Also, heretofore there has been a lack of fashioning a suitable dressing to carry out certain applications of these type of hydrogels. In this regard, prolonged usage of a hydrogel dressing often exceeded the absorptive ability of the dressing resulting in leakage of exudate from the wound causing a break in the integrity of the dressing thus exposing the wound to infection.

There is a need for a suitable dressing which is capable of keeping a wound moist while absorbing excess wound exudates. It is also desirable that such hydrogel dressing be bacteriostatic and able to maintain growth factors in wound sites and modulate infectious reactions. Further, there is a need to have such dressing be self-sustaining in a position for a predetermined period of time, e.g., several days, and which is substantially non-traumatic to the wound upon removal.

BRIEF SUMMARY OF THE INVENTION

It is an object to improve wound healing treatment.

It is a further object to improve dressings for wound healing applications.

It is another object to provide a therapeutic mask for treating facial wounds.

The present invention is directed to a therapeutic mask for application to a face of a patient suffering from having facial wounds. The therapeutic mask includes a relatively elastic substrate having a plurality of open surfaces defined therein of a predetermined size and spatially positioned with respect to one another to accommodate the patient's eyes, nose and mouth. The mask includes a hydrogel substance having a plurality of open surfaces defined therein of a predetermined size and spatially positioned with respect to one another to accommodate the patient's eyes, nose and mouth and complimentarily connected to the elastic substrate such that the respective eye, nose and mouth open surfaces align. The therapeutic mask further includes retaining straps connectable to the elastic substrate and of a size and configuration to extend about the head of the patient for supporting the therapeutic mask in a relatively fixed position on the patient's face.

Other objects and advantages will be readily apparent to those skilled in the art upon viewing the drawings and reading the detailed description hereafter.

DETAILED DESCRIPTION OF THE INVENTION

Figure 1:
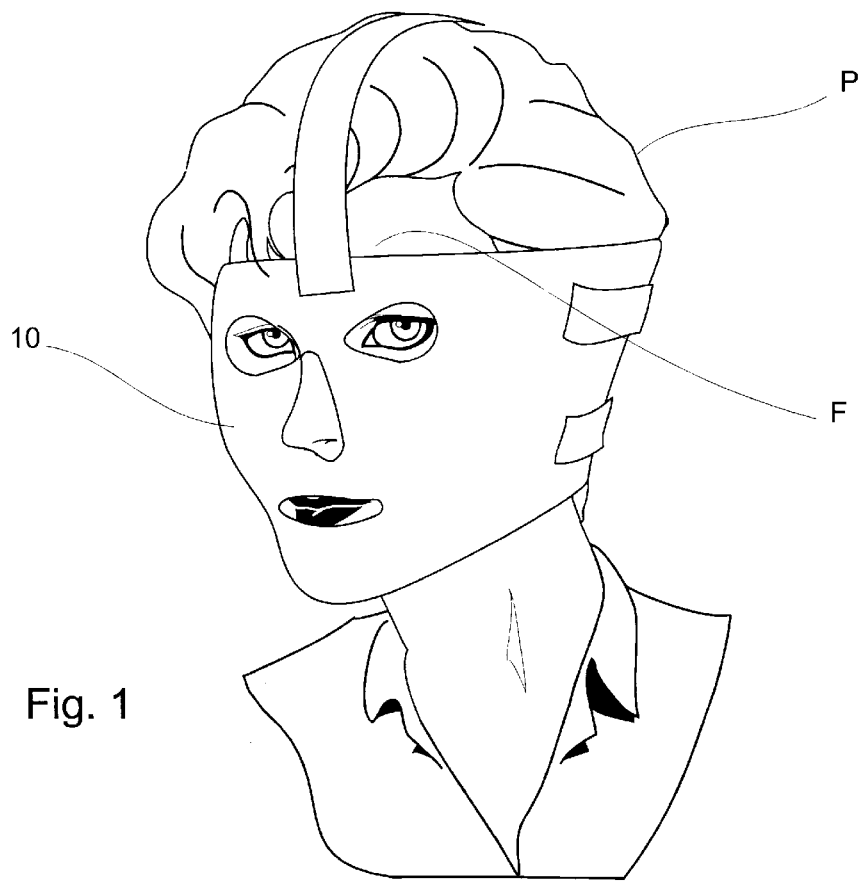
FIG. 1 is a perspective view of the present invention in use on a patient.
Figure 2:
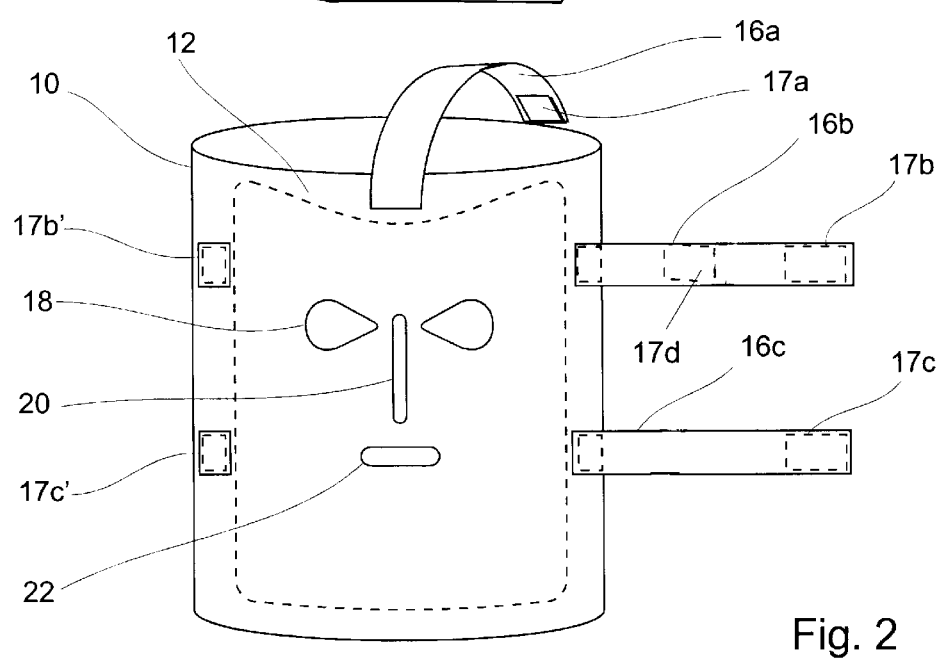
FIG. 2 is a front view of the present invention.
Figure 4:
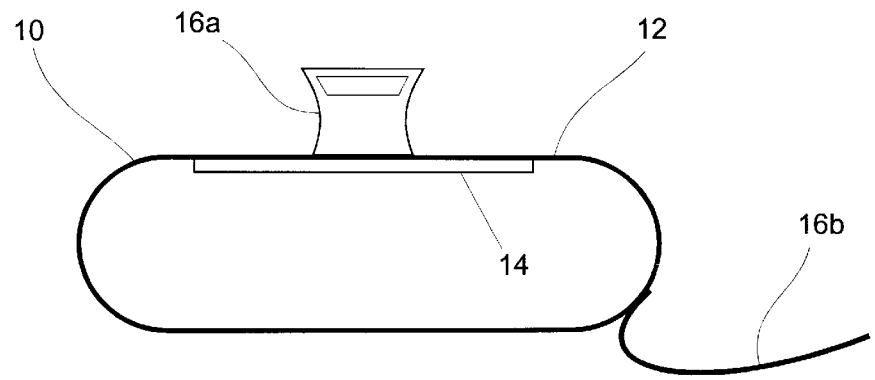
FIG. 4 is an end view of the present invention.
Figure 3:
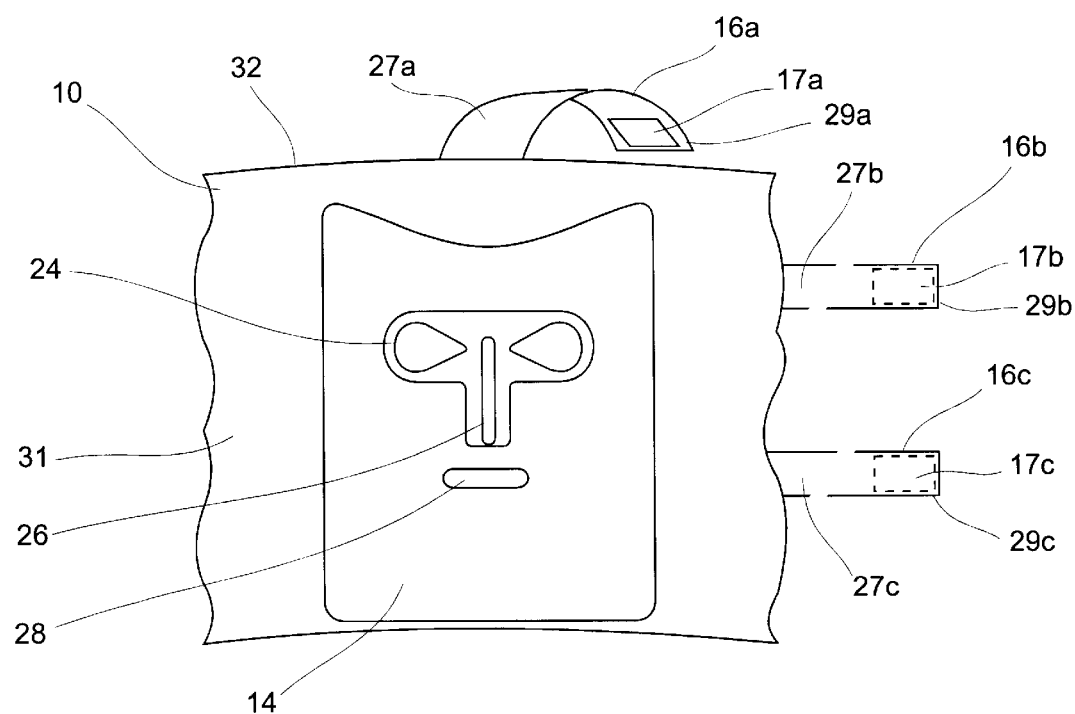
FIG. 3 is a back view of the present invention.

Referring now to the drawings, a therapeutic mask of the present invention is generally referred to by the numeral 10. The therapeutic mask 10 is designed for application to a face F of a patient P who suffers from facial wounds as a result of ulceration, surgical incision, laser treatment, chemical peel, burns, paryngocutaneous fistulas and/or resurfacing of the skin, for example.

The therapeutic mask 10 includes a slightly elastic substrate 12, a hydrogel material 14 and retaining straps 16. The hydrophillic gel 14 is connectedly applied to the substrate 12 so that the gel 14 sticks to the substrate 12.

The substrate 12 is preferably made of a fabric material, such as a spandex material, and is tubular to permit sliding the same over the head of the patient P. The substrate 12 should have sufficient elasticity to accommodate expansion which occurs during the absorption of the fluids in the hydrogel 14. Additionally, the substrate 12 should also be of sufficient strength and inelasticity to maintain the gel 14 in a relatively fixed position with respect to the substrate 12 as fluid is adsorbed. The substrate 12 has a plurality of open surfaces 18, 20 and 22 defined therein of a predetermined size and spatially positioned with respect to one another to accommodate the patient's eyes, nose and mouth, respectively.

The hydrogel 14 of the present invention is preferably one which has bacteriostatic properties and is highly absorptive. A blend of glycerine, water and polyacrylamide is found to be very useful in this regard having percentages in the amounts of 65–70 weight percent, 15–20 weight percent and 15–20 weight percent, respectively. The hydrogel 14 may include or be comprised of other substances such as ethylene glycol, propylene glycol, dimethyl oxide, dimethyl formamide, poly-2-hydroxyethelymethacrylate, or hydrocolloid with pectin or carboxymethyl cellulose, for example, the selection of which is predicated upon the degree of absorptivity required. The present invention permits usage of highly absorptive hydrogel components via its ability to retain the hydrogel proximate a predetermined location adjacent the wound site via the substrate 12 and retaining straps 16.

The hydrogel 14 also has a plurality of open surfaces 24, 26 and 28 defined therein of a predetermined size and spatially positioned with respect to one another to accommodate the patient's eyes, nose and mouth, respectively. These opening surfaces 24, 26 and 28 are complimentarily oriented on the substrate 12 such that the respective eye, nose and mouth open surfaces 18, 20 and 22, respectively, are aligned. The length and width of the hydrogel 14 should be sufficient to cover the face F but sufficiently less than the size of the substrate 12 such that upon expansion of the hydrogel 14, the hydrogel 14 will be retained between the confines of the substrate 12 and face F.

The retaining straps 16 are connected to the elastic substrate 12 via Velcro™ hook and loop fasteners 17 obtainable from the Velcro Corporation wherein an end 27 is connected to the substrate 12 in a fixed manner and another end 29 of the retaining straps 16 wrap about the back of the head of the patient P to fasten and secure the substrate 12 in place. Here, the retaining straps 16b and 16c interconnect to the sides 31 of the substrate 12 and the retaining strap 16a interconnect the top 32 of the substrate 12 and retaining strap 16b via Velcro™ hook and loop fasteners 17a and 17d. The retaining straps 16 are of a size and configuration to extend about the head of the patient for supporting the therapeutic mask in a relatively fixed position on the patient's face and have sufficiently sized Velcro™TM fasteners to accommodate varying sized heads. While the retaining straps 16 are shown as being connected to the substrate 12 in a particular embodiment, it will be readily apparent to one skilled in the art that other retaining configurations can be employed to carry out this aspect of the invention.

The above described embodiment is set forth by way of example and is not for the purpose of limiting the present invention. It will be readily apparent to those skilled in the art that obvious modifications, derivations and variations can be made to the embodiment without departing from the scope of the invention. Accordingly, the claims appended hereto should be read in their full scope including any such modifications, derivations and variations.

What is claimed is:

1. A therapeutic mask for application to a face of a patient suffering from facial wounds, which includes:

a relatively elastic substrate having a plurality of open surfaces defined therein of a predetermined size and spatially positioned with respect to one another to accommodate the patient's eyes, nose and mouth; and a hydrophillic hydrogel substance having a plurality of open surfaces defined therein of a predetermined size and spatially positioned with respect to one another to accommodate the patient's eyes, nose and mouth and complimentarily connected to said elastic substrate such that said eye open surfaces are oriented in an aligned manner, said nose open surfaces are oriented in an aligned manner and said mouth open surfaces are oriented in an aligned manner.

2. The therapeutic mask of claim 1, which further includes at least one retaining strap of a size and configuration to extend about the head of the patient for supporting the said therapeutic mask in a relatively fixed position on the patient's face.

3. The therapeutic mask of claim 2, wherein said retaining strap is removably connectable to said elastic substrate.

4. The therapeutic mask of claim 2, which is further characterized to include a plurality of retaining straps removably connectable to said elastic substrate.

5. The therapeutic mask of claim 1, wherein said hydrogel is characterized to be one of relatively high absorption and have bacteriostatic property.

6. The therapeutic mask of claim 5, wherein said hydrogel includes blend of glycerine, water and polyacrylamide.

7. The therapeutic mask of claim 6, wherein said hydrogel includes blend of glycerine in about 65–70 weight percent, water in about 15–20 weight percent and polyacrylamide in about 15–20 weight percent.

8. The therapeutic mask of claim 1, wherein said hydrogel is of a length and width sufficiently less than the length and width of said substrate such that said hydrogel is substantially retained between said substrate and the face of the patient upon expansion of said hydrogel due to adsorption.

* * * * *